United States Patent [19]

Hosoi et al.

[11] 4,065,475
[45] Dec. 27, 1977

[54] PROCESS FOR PREPARING CIS-EPOXYSUCCINIC ACID SALTS OF HIGH PURITY

[75] Inventors: Kazuo Hosoi; Norio Kawabe; Masaji Ohno, all of Kamakura, Japan

[73] Assignee: Toray Industries, Inc., Tokyo, Japan

[21] Appl. No.: 688,920

[22] Filed: May 21, 1976

Related U.S. Application Data

[63] Continuation-in-part of Ser. No. 605,552, Aug. 7, 1975, abandoned.

[51] Int. Cl.² .................................... C07D 301/12
[52] U.S. Cl. ........................................ 260/348.31
[58] Field of Search ............................. 260/348.5 L

[56] References Cited

U.S. PATENT DOCUMENTS

| 2,786,854 | 3/1957 | Smith et al. | 260/348.5 L |
|---|---|---|---|
| 2,833,788 | 5/1958 | Skinner et al. | 260/348.5 L |
| 3,156,709 | 11/1964 | Allan | 260/348.5 L |
| 3,629,144 | 12/1971 | Hahn et al. | 260/348.5 L |
| 3,769,339 | 10/1973 | Wagner et al. | 260/536 |
| 3,783,154 | 1/1974 | Wiley | 260/348.5 L |

FOREIGN PATENT DOCUMENTS

| 2,347,224 | 4/1974 | Germany | 260/348.5 L |

OTHER PUBLICATIONS

J. M. Church et al., Ind. & Eng. Chemistry, vol. 43, No. 8, (Aug. 1951), pp. 1780–1786.
G. Payne et al., Jour. Org. Chem., vol. 24, (1959), pp. 54–55.

Primary Examiner—Norma S. Milestone
Attorney, Agent, or Firm—Miller & Prestia

[57] ABSTRACT

High purity cis-epoxysuccinic acid and salts thereof are economically and systematically prepared by contacting an aqueous solution, obtained by reacting a maleic acid salt and hydrogen peroxide in the presence of a tungstate or molybdate catalyst under a specified condition, with a strongly basic Type II anion exchange resin.

8 Claims, 5 Drawing Figures

PROCESS FOR PREPARING CIS-EPOXYSUCCINIC ACID SALTS OF HIGH PURITY

RELATED APPLICATION

This application is a continuation-in-part of U.S. application Ser. No. 605,552 filed Aug. 7, 1975, now abandoned.

SUMMARY OF THE INVENTION

This invention relates to a systematic process for preparing cis-epoxysuccinic acid salts of high purity and, more particularly, to a recyclable system for the catalysts and the strongly basic anion exchange resins wherein the catalysts are used in an epoxidation reaction of maleic acid with hydrogen peroxide, and the anion exchange resins are used to remove the catalysts from the reaction products. A summary of the novel method embodied by this invention is set forth in Chart 1.

CHART 1

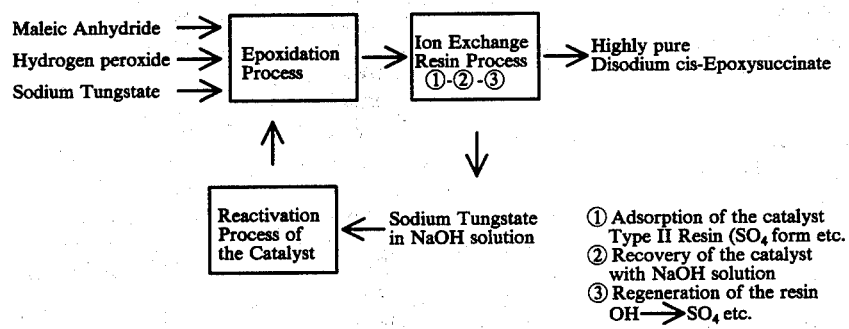

① Adsorption of the catalyst Type II Resin ($SO_4$ form etc.
② Recovery of the catalyst with NaOH solution
③ Regeneration of the resin OH→$SO_4$ etc.

DISCUSSION OF THE PRIOR ART

Epoxysuccinic acid is commercially valuable as an important intermediate in the production of tartaric acid and because it can be converted into dialkyl tin epoxysuccinates which are utilized as plasticizers-stabilizers for polyvinyl chloride (Bauley et al U.S. Pat. No. 2,972,595). Dialkyl tin epoxysuccinates can also be formed into cross-linkable epoxy-containing film forming polyamides (Campbell et al, J. Polymer, Sci., Pt. Al, 2525 (1963)) and are also useful as builders of cleansers (W. German Offenlegungsschrift No. 2,160,908).

However, epoxysuccinic acid prepared by conventional procedures generally contains heavy metal ion salts such as Os, Sr, Th, V. MO and W in concentrations of more than 100 ppm, and the recovery of the catalyst is not complete when these conventional procedures are employed. Therefore, these conventional procedures are not economical, and present both product safety and pollution hazards when utilized on a commercial scale. When epoxysuccinic acid is directly converted to optically active tartaric acid through an enzymatic process (U.S. Pat. No. 3,957,579), further purification of the product is required to remove the heavy metal ions that were used as catalysts. Thus, the preparation of tartaric acid by direct conversion of epoxysucininc acid is not economical.

The oxidation of maleic acid with hydrogen peroxide to yield an epoxide and/or a polyhydroxy compound is well known (Payne et al, Journal or Org. Chem., Volume 24, pages 54–55 (1959); Church et al, Ind. and Eng. Chemistry, volume 43, pp. 1780–1786 (1951). The production of such oxidation products by reaction of various ethylenic compounds and hydrogen peroxide in the presence of inorganic catalysts such as Os, Sr, Th, V, MO, W, V and Se has been reported. However, the use of such catalysts has not been practical for various reasons. First, these catalysts are expensive and as such it is essential to recover them. Moreover, the usual methods for recovery are generally cumbersome and costly, particularly when relatively high concentrations of the catalysts are required. In the second plate, product and environmental contamination by the catalyst provides not only a legal problem, but also an important commercial problem to overcome.

Another process for oxidizing maleic acid with hydrogen peroxide uses an insoluble organometallic compound as a catalyst. This process requires a large amount of resin to obtain a practical reaction rate and therefore is not economical. (G. G. Allan, USP 3,156,709). Cis-epoxysuccinic acid prepared by Allan's method is about 95% pure, as organic acid and product always contain a concentration of tungstate ion greater than 100 ppm as shown in reference Example 1. This result shows that a further purification step is required to obtain a pure product.

The processes which use basic ion exchange resins to remove catalysts from epoxidation products are shown by G. W. Smith (U.S. Pat. No. 2,786,854) and A. Iguchi (CA, 51, 9255). P. H. Baker (U.S. Pat. No. 2,968,527) and G. A. Hahn (U.S. Pat. No. 3,629,144) developed their own method to use sodium chloride and sodium bicarbonate, respectively, to recover and to utilize effectively the tungstic acid catalyst in conjunction with such oxidations. However, we have now found that simple applications of these methods to the epoxidation of maleic acid with hydrogen peroxide do not form epoxysuccinic acid of high purity and cannot accomplish an effective recycling of the catalyst.

OBJECTS OF THE PRESENT INVENTION

Therefore, an object of this invention is to overcome the aforementioned problems and disadvantages of the prior art conventional processes.

A further object of this invention is to provide a highly pure cis-epoxysuccinic acid in salt form, which is practically free of tungstate or molybdate, and which is subjected to an enzymatic reaction to produce optically active tartaric acid.

Another object of this invention is to recover the expensive catalyst without practical loss, and to reuse it for the epoxidation reaction. The cis-epoxysuccinic acid prepared by this invention is more than 99% pure as an acid and contains less than 10 ppm of tungstate or molybdate ions.

Other objects and advantages of this invention will become apparent hereinafter and in the drawings.

DRAWINGS

The drawings (FIGS. 1-5) are graphs showing results obtained in accordance with test runs reported in the Examples.

DETAILED DESCRIPTION OF THE INVENTION

Figure 1:
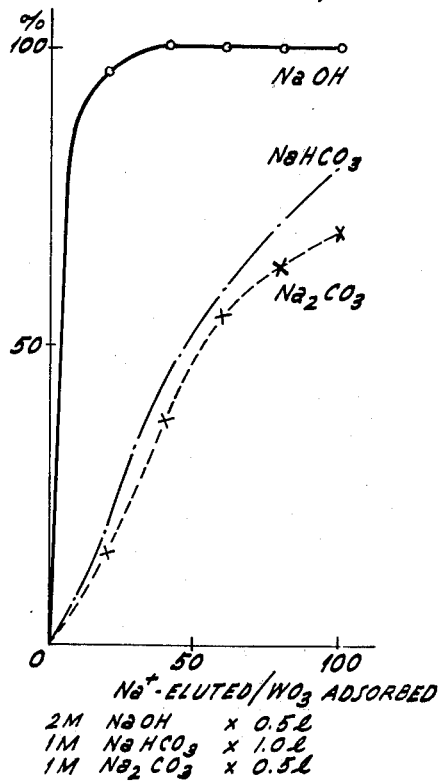

In accomplishing these objects, the aqueous solution of cis-epoxysuccinic acid salt, which is obtained by the reaction of a maleic acid salt and hydrogen peroxide in the presence of a tungstate or molybdate catalyst, is brought into contact with a strongly basic anion exchange resin to selectively adsorb the catalyst. The adsorbed catalyst is eluted by an aqueous solution of alkali metal hydroxide, and the resulting mixture containing the recovered catalyst is repeatedly used for epoxidation after a specific treatment, as mentioned later, is performed. In general, the reaction conditions of the epoxidation reaction are as follows.

The maleic acid salt and hydrogen peroxide are used stoichiometrically; more preferably, 1-1.3 mole equivalent of hydrogen peroxide to maleic acid is used.

The pH of the reaction system is within the range of about 2-7, more preferably 3-6. The reaction temperature is about 40°-80° C, more preferably 50°-70° C.

The preferable maleic acid salts include the alkali metal salt and the calcium salt. More preferably, the maleic acid salt is selected from the group consisting of the sodium salt, the potassium salt and the calcium salt, and mixtures thereof.

Such a maleic acid salt may be formed in the reaction system by adding maleic acid or maleic anhydride into a reaction medium containing an alkali metal hydroxide or the like.

The preferable catalysts contain alkali metal salts of tungstic acid and molybdic acid, such as sodium tungstate dihydrate and sodium molybdate dihydrate, for example.

The catalysts are used in a normal catalytic amount, preferably about 0.001-0.1 mole to 1 mole of maleic acid.

According to this invention, it has been found that tungstate or molybdate catalysts are selectively and completely adsorbed from the solution of the epoxidation product (which is a strong electrolyte) by a strongly basic anion exchange resin. We have further found that the adsorption capability of the catalysts on such resin is strongly dependent on the pH of the solution. The catalyst is best adsorbed at a pH lower than about 7, preferably at a pH of about 3 - 6.9, more preferably at a pH 5- 6.5, and less adsorbed at a neutral pH and least adsorbed at a pH higher than 7.

The most highly preferred resins are the well known and commercially available quarternary ammonium resins formed by the amination, with dimethyl ethanolamine (Type-II), of a chloromethylated copolymer of styrene and divinylbenzene. Although basic ion exchange resins employed (Type-I) tertiary amines as the aminating agents may be used, these Type-I resins lead to formation of a cis-epoxysuccinic acid metal salt product that has a higher catalyst content than the product formed by the use of Type-II resins. These results are clearly indicated in Table 2.

Although there are many different types of resins such as the gel-type, porous-type, the macro-porous-type, the resins may be used in any form. A granular form corresponding to about 20 to 100 mesh is generally satisfactory.

Anions of the resins are those in the neutralized form, or salt form, which are obtained by neutralizing an hydroxyl group of the resin. Any kind of neutralized anion may be used. Preferable anions used in this invention are: sulfate, chloride, organic carboxylate anions such as R—COO— (wherein R is any alkyl group), or epoxysuccinic anions.

In the method of this invention, the space velocity used to elute the adsorbed catalysts from the column resin is determined from a point of view of efficiency of removal of the catalyst, and of economy of time (usually SV = 0.5 - 4).

The objects of this invention are well accomplished by effecting the removal and recovery of the catalysts on a column resin.

In the method of this invention, about a 2 to 10 mole equivalent of the total anion exchange capacity of the strongly basic anion exchange resin is satisfactory when used to adsorb 1 mole of tungstic or molybdic acid salts. However, the relative amounts ae dependent on many factors such as: forms, degree of crosslinking, particle size, column type, space velocity and concentration of catalysts.

Thus, the objects of this invention are most effectively achieved by using a one-step resin-column tower or, if necessary, a multistage resin-column tower to provide alkali metal salts of pure cis-epoxysuccinic acid after the removal of the catalysts by complete adsorption of the catalysts on the resin.

The next step of this invention relates to recovering of the adsorbed catalysts in reusable form from the resin, as well as regeneration of the strongly basic anion exchange resin in reusable form. The recovered catalysts are reused for epoxidation as mentioned above. In accomplishing the recovery of the adsorbed catalysts, alkali metal hydroxide salts are preferably used. One of the most important features of this invention comprises reusing not only the recovered catalysts in the epoxidation reaction, but also reusing the basic solution used in recovering the catalysts. Thus, maleic acid or maleic anhydride and hydrogen peroxide are added to the solution which was used for the recovery of the catalysts. Of course, new catalyst or new base is added to the solution, if necessary. The alkali metal hydroxide salt solution preferably contains sodium hydroxide and potassium hydroxide.

The use of alkali metal carbonate solutions containing either sodium carbonate or sodium bicarbonate to recover the adsorbed catalysts were found inferior to sodium hydroxide solution as shown in Example 5 and summarized in FIGS. 1 - 4. Accordingly, the present invention is an inventive improvement over Hahn's method (U.S. Pat. No. 3,629,144).

The solution eluted at the beginning of the catalyst recovery step may contain a very small amount of the alkali metal salts of epoxysuccinic, racemic tartaric and maleic acid. However, the solution may be used for the epoxidation reaction after the removal of the tartaric acid by the addition of calcium ions to the solution. Indeed, the inclusion of racemic tartaric acid or its salts in the solution would greatly hinder the catalytic acitivity in the next epoxidation reaction. However, after the removal of the racemic tartaric acid and its salts from the solution, the catalytic activity is restored.

The calcium-treatment is preferably used for the sake of efficiency of the catalyst and to reduce reaction time. It is well known that tartaric acid forms an insoluble calcium salt and that calcium tungstate is hardly soluble in an aqueous solution. When calcium ions are added to the recovery solution mentioned above, the loss of the catalyst is considerable. Therefore, we have found an optimum condition wherein racemic tartaric acid is selectively removed, such a selective removal of racemic tartaric acid and the reuse of the catalyst are preferably conducted as explained below and in Examples 6-10 and FIG. 5.

Basically, calcium ions in an amount greater than 1 mole equivalent (more preferably about 1.4-2.0 mole equivalent) of dissolved racemic tartaric acid or its salt, are added into the catalyst recovery solution. The pH range should be kept at 7.0-8.5 to precipitate calcium tartrate, as summarized in FIG. 5.

The preferable calcium ion sources include calcium hydroxide, calcium oxide, calcium maleate, calcium sulfate and calcium dichloride.

The concentration of the eluent used for recovery of the catalyst ranges from about 1 to 6 normal, more preferably about 2 – 3 normal.

In this invention, a high percentage recovery of the catalyst as well as a high percentage regeneration of the exchange resin are accomplished at the same time. Furthermore, as indicated before, it has been found that the Type II-strongly basic anion exchange resin is remarkably preferred to the Type I- exchange resin.

The cost of the basic solution or eluent used in recovering the adsorbed catalysts and regenerating the resin is inexpensive since the solution is used as a part of the epoxidation reaction. In this invention, such amount of basic solution of eluent should correspond to, or be slightly less than, the amount necessary for the next epoxidation reaction. According to the novel method of the present invention, the solution of alkali metal hydroxide and the recovered catalysts contained in the solution are reused for epoxidation, so that if the amount of the base and catalyst is within the necessary quantity for epoxidation, total balance of the reactants is ideally accomplished carrying out a most economical reaction.

In order to accomplish this remarkable effect, the Type II-strongly basic exchange resin is most preferably used to recover the adsorbed catalysts efficiently. The eluent or basic solution regenerates the exchange resin for reuse within an amount which satisfies the economic conditions mentioned above. Thus, pure cis-epoxysuccinic acid is obtained even after many recycles of the catalysts and exchange resins as shown in Table 2. As for the recovered catalysts, they can be used for the next epoxidation.

However, in order to obtain the most efficient and constant use of the catalysts, treatment of the catalyst recovery solution with calcium ions is desirable.

In order to remove hydrogen peroxide, the pH of the epoxidation product solution is first adjusted to about 8 – 9 to decompose it, and then the pH is readjusted to about 3 – 7 for contact with the exchange resin.

When compared with Allan's, Hahn's and other methods previously mentioned, the present invention displays a remarkable advance in the art. Allan's method requires 2 to 7 times more catalyst than the homogeneous reaction, and also requires a large amount of exchange resin, which is quite expensive and fragile in the hydrogen peroxide solution.

However, it has now been realized that these disadvantages can be avoided by the removal and recovery of the catalyst and by the regeneration of the exchange resin, thus producing highly pure cis-epoxysuccinic acid or its alkali salt in a quantitative yield.

Finally, it should be mentioned here that highly pure cis-epoxysuccinic acid or its salt obtained by this systematic invention affords a remarkable effect on the purity of -L(+)- tartaric acid converted from the cis-epoxysuccinic as produced by this invention, through an enzymatic process, as shown in Example 11 and summarized in Table 3.

REFERENCE EXAMPLE 1

According with Allan's procedure*, an organometallic catalyst was prepared from a strongly basic anion exchange resin "Amberlite" IRA 400 and sodium tungstate dihydrate ($Na_2WO_4 \cdot 2H_2O$). The tungsten trioxide ($WO_3$) content of the dried catalyst was 3.8%.

*Journal of Catalysis Vol. 19, p. 256-263 (1970) by G. G. Allan et al. U.S. Pat. No. 3,156,709 by G. G. Allan The resin-hydrogen tungstate catalyst thus obtained (12 ml) was used for the epoxidation of maleic acid (11.6 g, 0.10 mole). Disodium cis-epoxysuccinate was obtained in about 95% purity and contained 0.02 millimoles of tungstate. The tungstate content of the cis-epoxysuccinate thereby produced was found to be 200 ppm.

Using the recovered resin catalyst once again, the second epoxidation of maleic acid (11.6 g, 0.10 mole) produced disodium cis-epoxysuccinate having about 95% purity, and containing 0.017 millimoles of tungstate.

Next, the reused resin catalyst was placed in a column (12 mm × 300 mm). An aqueous solution (80 ml) of disodium cis-epoxysuccinate (17.6 g, 0.1 mole) free from tungstate was adjusted to pH 5 by the addition of sulfuric acid, and then passed through the column. The effluent contained 0.028 millimoles tungstate and the tungstate content of the disodium cis-epoxysuccinate was found to be 300 ppm.

These results are shown in Table 1 and compared with those of this invention.

TABLE 1

|  | Allan's method | Method of this invention |
|---|---|---|
| Purity of cis-epoxysuccinate | about 95% | 99-100% |
| Contamination of tungstate | 100-200 ppm | 0-5 ppm |

EXAMPLE 1

98 g (1.0 mole) of maleic anhydride in 300 ml of water were reacted with 3.3 g (0.01 mole) of sodium tungstate, 137 g (1.2 moles) of hydrogen peroxide (30%) and 12 N sodium hydroxide for 2.5 hours at 65° C and pH 5.

The reaction solution was freed of excess hydrogen peroxide by increasing the alkalinity of the solution to pH 8.

It was found by analytical gas chromatography that the conversion of maleic acid to cis-epoxysuccinic acid was greater than 99.5%.

The resulting solution was adjusted to pH 5 with 6 N sulfuric acid, and had a volume of 0.75l. The solution was then passed through a column (15 mm × 500 mm) packed with 50 ml of a strongly basic anion exchange resin (Type II) "DIAION" PA 410 (SO₄ form) at a rate of 50 ml/hr. (SV = 1) and washed with 50 ml of water.

The combined effluent was adjusted to pH 7.5. The removal efficiency of the tungstate catalyst from the cis-epoxysuccinic acid product was found to be more than 99.95%, and the yield of tungstate-free disodium cis-epoxysuccinate was 97%. The purity of cis-epoxysuccinic acid to total organic acids in the solution was more than 99.5%.

The tungstate catalyst was eluted from the column with 400 ml of 3 N sodium hydroxide solution and form, a (Type I) "DIAION" PA 310 in the sulfate form, and (Type I) "DIAION" PA 310 in the hydroxyl form, were employed instead of (Type II) "DIAION" PA 410 in the sulfate form as utilized in Example 1. For each resin, the removal efficiency of tungstate from an epoxidation solution of disodium cis-epoxysuccinate, the recovery yield of tungstate from the resin by using 400 ml of 3 N sodium hydroxide solution and the second removal efficiency of tungstate using the regenerated resin were examined and the results were summarized in Table 2.

(Tungstate 2

REMOVAL EFFICIENCIES AND RECOVERY YIELDS OF TUNGSTATE

| Example No. | Resin (form of anion) (Type) | Removal Run | Removal Efficiency | (Tunstate content in disodium cis-epoxysuccinate) | Recovery yield of Tungstate from Resin |
|---|---|---|---|---|---|
| 1 | PA 410 (SO₄) (Type II) | 1st | 99.95~100% | (0~5 ppm) | 99~100% |
|   |   | 2nd | 99.95~100% | (0~5 ppm) |   |
| 2 | PA 410 (OH) (Type II) | 1st | 99.4% | (60 ppm) | 99% |
|   |   | 2nd | 99.4% | (60 ppm) |   |
| 3 | PA 310 (SO₄) (Type I) | 1st | 99.95~100% | (0-5 ppm) | ~95% |
|   |   | 2nd | 97% | (300 ppm) |   |
| 4 | PA 310 (OH) (Type I) | 1st | 99.4% | (60 ppm) | ~95% |
|   |   | 2nd | 97% | (300 ppm) |   | washed with water.

The effluent obtained by first contacting the column with 400 ml of 3 N sodium hydroxide solution and then washing the resulting mixture with water (hereinafter referred to as the first effluent), contained 8 millimoles of tungstate, 2 millimoles of maleate, 10 millimoles of racemic tartrate, 13 millimoles of cis-epoxysuccinate and 32 millimoles of sodium hydroxide. Two millimoles of tungstate were recovered from the washed "product" solution (350 ml). Thus, the tungstate was recovered from the resin quantitatively.

The first effluent was adjusted to pH 8 by the addition of 2.55 g (26 millimoles) of maleic anhydride and 3.44 g (20 millimoles) of calicum sulfate (CaSO₄.2H₂O) to the solution. After stirring for 2 hours, the precipitate was removed by filtration and washed with 20 ml of water.

The precipitate contained 2.6 g (10 millimoles) of racemic calcium tartrate (C₄H₄O₆Ca.4H₂O) and a small amount of calcium sulfate.

The filtrate contained 7.9 millimoles of tungstate, 28 millimoles of maleate, 13 millimoles of cis-epoxysuccinate and about 20 millimoles of sulfate ions.

A second epoxidation reaction was carried out using the recovered catalyst at 65° C and pH 5.

Maleic anhydride (95.45g, 0.974 moles) was dissolved in the combined solution of the first effluent (free from the racemic tartrate filtrate), and then reacted with 137 g (1.2 moles) of hydrogen peroxide (30%).

The conversion of maleic acid to cis-epoxysuccinic acid was found to be greater than 99.5%.

The resin in the hydroxyl form was converted to its sulfate form by eluting 100 ml of 1N sulfuric acid and then washing the eluted resin with water.

The tungstate was removed from the second reaction product solution using the regenerated resin obtained above. The removal efficiency was found more than 99.95%.

The resin in the column was regenerated and used repeatedly at the same time.

The recovery and reuse of the catalyst were carried out in a similar manner as described before.

EXAMPLES 2-4

There samples of a strongly basic anion exchange resins: (Type II) "DIAION" PA 410 in the hydroxyl

EXAMPLE 5

Three columns, each packed with 50 ml of "DIAION" PA 408 strongly basic anion exchange resin (Type II), each of which columns adsorbed 10 m moles of tungstate at an acid pH, were separately treated with different regenerants. These regenerants were chosen from the group consisting of 0.5l of 2N sodium hydroxide solution, 1l of 1N sodium bicarbonate solution, and 0.5l of 1M sodium carbonate solution.

The tungstate content in each of the three effluents was measured photometrically by $SnCl_2$-KSCN method. It was found that sodium hydroxide removed quantitatively the adsorbed tungstate, while sodium bicarbonate and sodium carbonate removed only 80% and 70%, respectively.

The results of recovery of the tungstate are shown in FIG. 1.

Figure 2:
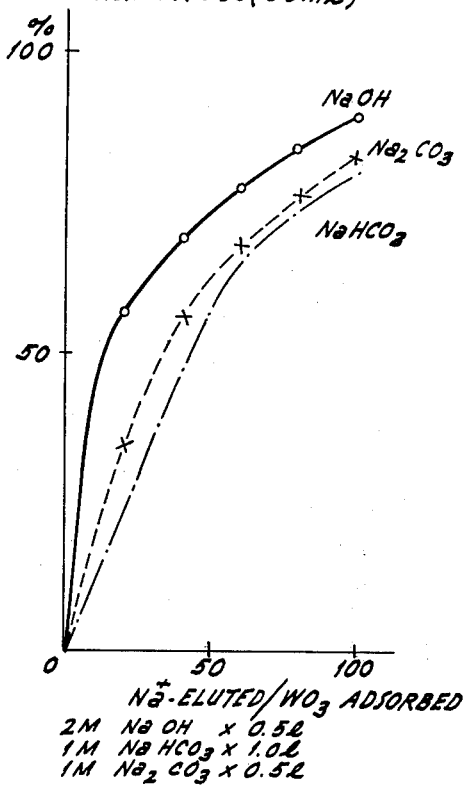

Three columns, each packed with 50 ml of "DIAION" PA 308 strongly basic anion exchange resin (Type I), each of which columns adsorbed 10 m moles of tungstate equivalently, were separately treated in the similar manner mentioned above. Sodium hydroxide, sodium bicarbonate and sodium carbonate removed 89%, 80% and 83% of the tungstate content, respectively. The results of recovery of the tungstate are shown in FIG. 2.

Figure 3:
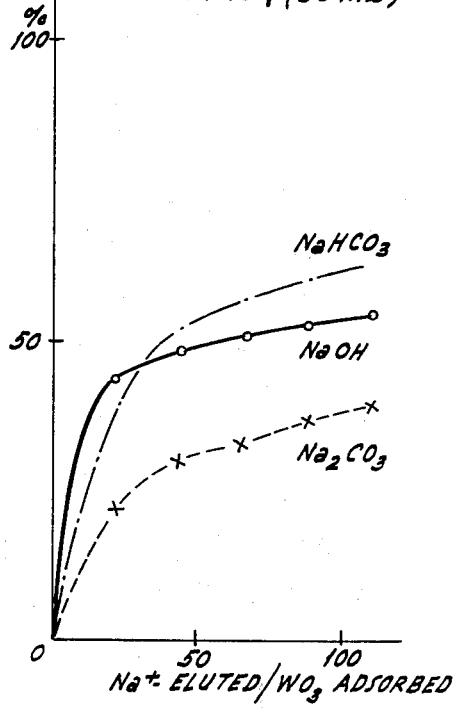

Three columns, each packed with 50 ml of "Amberlite" IRA 904, strongly basic anion exchange resin (Type I, macroreticular structure), each of which columns adsorbed 9.1 m moles of tungstate, were separately treated in the similar manner mentioned above. Sodium hydroxide, sodium bicarbonate and sodium carbonate removed 54%, 63% and 39% of the tungstate content, respectively. The results of recovery of the tungstate are shown in FIG. 3.

Figure 4:
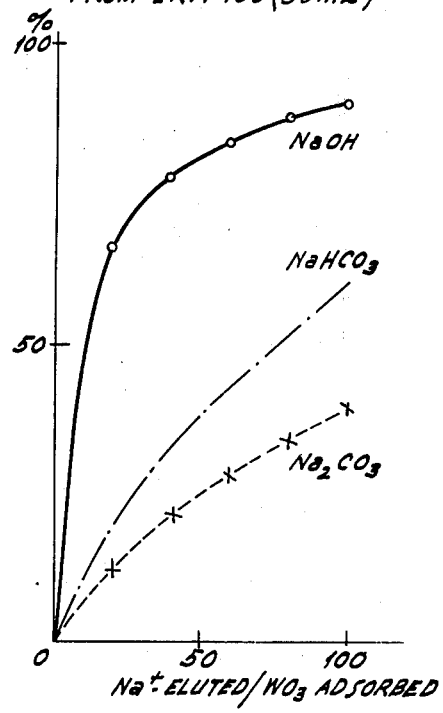

Three columns, each packed with 50 ml of "Amberlite" IRA 400 strongly basic anion exchange resin (Type I, gel type), each of which columns adsorbed 10 m moles of tungstate equivalently, were separately treated in the similar manner mentioned above. Sodium hydroxide, sodium bicarbonate and sodium carbonate removed 90%, 60% and 40% of the tungstate respectively. The results of recovery of the tungstate are shown in FIG. 4.

EXAMPLE 6

The effect of the pH and reaction duration variants upon both the efficiency of racemic tartrate removal and tungstate loss was studied as follows:

An aliquot was taken from the first effluent in Example 1 and adjusted to a respective pH by addition of maleic acid. Investigated pH values were 5, 6, 7, 8, 9, 10, 11 and 13.

Figure 5:
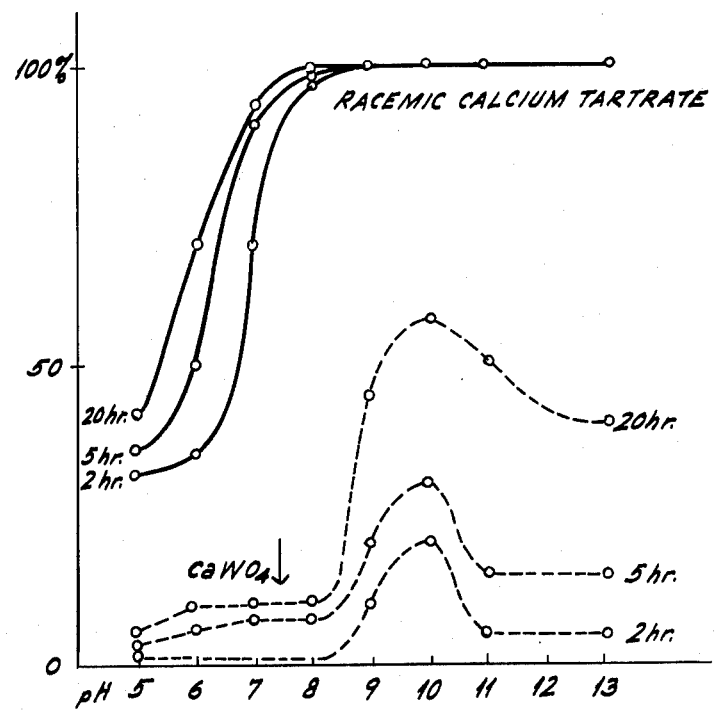

To each solution, a two mole equivalent of calcium sulfate to racemic tartrate was added and the solution was stirred. A small amount of the solution was taken and examined for racemic tartrate and tungstate content. The results are shown in FIG. 5. The removal of racemic tartrate was very efficient above pH 7.5. On the other hand, the tungstate loss was negligible below pH 8.5 at a time duration of 2 hours, but tungstate loss increased considerably above pH 8.5, and at longer durational periods.

EXAMPLE 7

When the tungstate recovered after a calcium ion treatment at pH 6 was used for the next epoxidation, the conversion of maleic acid to cis-epoxysuccinate was 98%. The result shows that the purity of the product is inadequate. As shown in FIG. 1, the recovery yield of tungstate was 99%, but not enough racemic tartrate was removed.

EXAMPLE 8

Removal of racemic tartrate was carried out at a pH 9 instead of pH 6 as in Example 7. The recovery yield of tungstate was 90%. The conversion of maleic acid to cis-epoxysuccinic acid in the next epoxidation was 98.5%.

EXAMPLE 9

The first effluent of the recovered catalyst eluted from "DIAION" PA 410 was directly reacted with calcium sulfate at pH 13. The recovery yield of tungstate was 95%.

EXAMPLE 10

The recovered catalyst was used for the second epoxidation reaction without removal of racemic tartaric acid of the first effluent. The conversion of maleic acid to cis-epoxysuccinic acid in the second reaction was found to be about 98%.

EXAMPLE 11

Three samples of disodium cis-epoxysuccinate solution containing different amount of tungstate were separately converted to d-tartrate by treatment with a microbiorganism (FERM-P 2507) which has the ability to convert cis-epoxysuccinate to d-tartrate selectively. Disodium d-tartrate enzymatically prepared was converted to calcium d-tartrate, followed by acid-treatment with sulfuric acid to afford d-tartaric acid. The tungstate contents in the product and the starting material are compared in Table 3.

TABLE 3

| Tungstate contents in disodium cis-epoxysuccinate | Tungstate contents in d-Tartaric acid |
| --- | --- |
| 5 ppm | below 0.1 ppm |
| 50 ppm | 5 – 10 ppm |

TABLE 3-continued

| Tungstate contents in disodium cis-epoxysuccinate | Tungstate contents in d-Tartaric acid |
| --- | --- |
| 300 ppm | 10 – 100 ppm |

EXAMPLE 12

2.42 g. (0.01 mole) of sodium molybdate dihydrate were employed instead of the 3.3g. (0.01 mole) of sodium tungstate in Example 1.

The conversion of maleic acid to cis-epoxysuccinic acid in the first reaction was found to be more than 99.5%. The removal of molybdate was carried out in a similar manner to that utilized in Example 1.

The effluent afforded disodium cis-epoxysuccinate free of molybdate. The molybdate catalyst, recovered from the resin in a similar manner to that utilized in Example 1, was used for the second epoxidation reaction.

The conversion in the second reaction was found to be more than 99.5%. The resin was regenerated and used repeatedly.

We claim:

1. A continuous process for preparing a highly pure cis-epoxysuccinic acid salt, comprising the steps of:
   a. conducting an epoxidation reaction by contacting and reacting a maleic acid salt with hydrogen peroxide in the presence of a tungstate or molybdate catalyst to form an aqueous epoxidation reaction solution;
   b. contacting said aqueous epoxidation reaction solution with a Type II strongly basic anion exchange resin in the neutralized form at a pH lower than about 7 to selectively adsorb said catalyst;
   c. contacting said resin with an alkali metal hydroxide to recover said catalyst in the form of an aqueous solution,
   d. treating said recovered catalyst solution with a calcium ion source at a pH of about 7.0–8.5, and
   e. adding maleic acid or maleic anhydride and hydrogen peroxide into said recovered catalyst solution to form another epoxidation reaction solution whereby the catalyst is recycled and the resin is regenerated to provide a continuous process.

2. A process according to claim 1 in which the maleic acid salt is selected from the group consisting of the sodium, potassium and calcium salts of maleic acid.

3. The process defined in claim 1, in which said epoxidation reaction is conducted at a pH of about 2–7, and then the pH of said resulting epoxidation reaction solution is adjusted to about 8–9, to decompose said hydrogen peroxide, and then the pH of said resulting epoxidation reaction solution is readjusted to about 3–7 before step (b) is started.

4. A process according to claim 1 in which the tungstate or molybdate catalyst is an alkali metal salt of tungstic acid or molybdic acid.

5. A process as recited in claim 1, wherein the concentration of alkali metal hydroxide is about 1 to 6 N.

6. A process as recited in claim 1, wherein said alkali metal hydroxide is chosen from the group consisting of sodium hydroxide, and potassium hydroxide.

7. A process as recited in claim 1, wherein said calcium ion source is selected from the group consisting of calcium hydroxide, calcium oxide, calcium maleate, calcium sulfate, and calcium dichloride.

8. A continuous process for preparing a highly pure cis-epoxysuccinic acid salt, comprising the steps of:
   a. conducting an epoxidation reaction by contacting and reacting a maleic acid salt with hydrogen peroxide in the presence of a tungstate or molybdate catalyst to form an aqueous epoxidation reaction solution;
   b. contacting said aqueous epoxidation reaction solution with a Type II strongly basic anion exchange resin in the neutralized form at a pH lower than about 7 to selectively adsorb said catalyst;
   c. contacting said resin with an alkali metal hydroxide to recover said catalyst in the form of an aqueous solution;
   d. treating said recovered catalyst solution with calcium sulfate at a pH of about 7.0–8.5 so as to precipitate calcium racemic tartrate, and then
   e. adding maleic acid or maleic anhydride and hydrogen peroxide into said recovered catalyst solution to form another epoxidation reaction solution, whereby the catalyst is recycled and the resin is regenerated so as to provide a continuous process.

* * * * *